United States Patent [19]

Takeuchi

[11] Patent Number: 5,150,062

[45] Date of Patent: Sep. 22, 1992

[54] ELECTROSTATIC CAPACITANCE SENSING CIRCUIT

[75] Inventor: Kiyoshi Takeuchi, Yokohama, Japan

[73] Assignee: Nissan Motor Co., Ltd., Yokohama, Japan

[21] Appl. No.: 634,240

[22] Filed: Jan. 2, 1991

[51] Int. Cl.[5] .............................................. G01N 27/22
[52] U.S. Cl. .................................... 324/675; 324/682; 340/620
[58] Field of Search ....................... 324/668, 675, 682; 73/304 C; 340/620

[56] References Cited

U.S. PATENT DOCUMENTS

| | | | |
|---|---|---|---|
| 3,046,479 | 7/1962 | Mead | 324/668 |
| 3,714,560 | 1/1973 | Farr | 324/668 |
| 4,002,996 | 1/1977 | Klebanoff | 324/668 |
| 4,050,016 | 9/1977 | Marsh | 324/668 |

FOREIGN PATENT DOCUMENTS 44-17838 8/1969 Japan .
57-7010 2/1982 Japan .

*Primary Examiner*—Kenneth A. Wieder
*Assistant Examiner*—Jose M. Solis
*Attorney, Agent, or Firm*—Foley & Lardner

[57] ABSTRACT

The electrostatic capacitance sensing circuit comprises a resonance circuit composed of an electrode capacitance formed by a substance to be measured and sandwiched between two opposing electrode plates and an inductance at least part of which is connected in parallel to the electrode capacitance; an active element (e.g. transistor) for constituting an oscillator in cooperation with the resonance circuit; and in particular a capacitor connected between the resonance circuit and the active element. Since a dc bias voltage of the active element is substantially not applied to the electrode plates, it is possible to prevent electrolytic corrosion of the electrode plates due to electromotive force generated between the electrode plates when ions are resolved into the substance to be measured and therefore the substance changes to an electrolytic solution.

15 Claims, 8 Drawing Sheets

ELECTROSTATIC CAPACITANCE SENSING CIRCUIT

BACKGROUND OF THE INVENTION

1. Field of the Invention

The present invention relates to a sensor circuit for sensing a dielectric constant of a substance to be measured or a concentration of a specific component, and more specifically to an electrostatic capacitance sensing circuit using an oscillator whose frequency changes according to an electrode capacitance formed by a substance to be measured and sandwiched between two opposing electrode plates.

2. Description of the Prior Art

FIG. 1(a) shows a prior-art Clapp oscillator capacitance sensing circuit, which is disclosed in Japanese Published Examined (Kokoku) utility Model Appli. No. 57-7010, and FIG. 1(b) is an equivalent circuit thereof.

The electrode 1A is disposed within a vessel 3 in which a substance 2 to be measured is put so as to form an electrode capacitor 1. The substance 2 to be measure is a mixture of gasoline (the dielectric constant or the relative permittivity: $\epsilon/\epsilon_0 \approx 2$) and methanol $\epsilon/\epsilon_0 \approx 30$), by way of example. The dielectric constant $\epsilon_1/\epsilon_0$ of this mixture changes according to the mixture ratio of gasoline to methanol. Further, the electrostatic capacitance $C_1$ between the electrode plates 1A changes roughly in proportion to the dielectric constant $\epsilon_1/\epsilon_0$ of the substance 2 to be measured, and therefore can be expressed as $$C_1 = \frac{A}{d} \epsilon_1 \text{ (pF)} \quad (1)$$

where $A(cm^2)$ denotes each opposing area of the electrode plates; $d(cm)$ denotes the distance between the two electrode plates; and $\epsilon_0 = 8.854 \times 10^{-14}$ (F/cm).

FIG. 1(c) shows the relationship between the electrostatic capacitance $C_1$ and the concentration M (by volume %) of methanol. The electrostatic capacitance $C_1$ formed by a substance 2 between a pair of the electrode plates 1A is referred to as electrode capacitance $C_1$, hereinafter.

The well-known Clapp oscillator shown in FIG. 1(a) is mainly composed of a resonance circuit and a transistor 9.

The resonance circuit is composed of an inductance (a coil) 6, four fixed capacitors 4, 5, 7 and 8, and an electrode capacitor 1, as depicted in FIG. 1(a). Further three biasing resistors 10, 11 and 12 are connected to the transistor 9 to apply appropriate bias voltages to the base and the emitter of the transistor 9.

Since the electrode capacitor 1 and capacitor 4 are connected in series; the two capacitors 7 and 8 are also connected in series; and further the capacitor 5 is connected in parallel to the two series-connected capacitors 1, 4 and 7, 8, the oscillation frequency $f_0$ of this Clapp oscillator can be expressed as $$f_0 = \frac{1}{2\pi \sqrt{L_6 \left( C_5 + \frac{C_1 C_4}{C_1 + C_4} + \frac{C_7 C_8}{C_7 + C_8} \right)}} \quad (2)$$

where $C_1$ denotes the electrode capacitance; $C_4$, $C_5$, $C_7$ and $C_8$ denote electrostatic capacitances of the capacitors 4, 5, 7 and 8; and $L_6$ denotes the inductance of the coil 6, as indicated in the equivalent circuit shown in FIG. 1(b).

The above expression 2 indicates that the Clapp oscillator frequency changes in inverse proportion to the electrode capacitance $C_1$. Further, in FIG. 1(a), the emitter output signal of the transistor 9 is applied to the F-V converter 14 via a capacitor 13 so that an output voltage E(v) can be changed according to the oscillator frequency $f_0$. Therefore, it is possible to measure the mixture ratio of gasoline and methanol on the basis of the output voltage E(v).

FIG. 2 shows a classical Hartley oscillator capacitance sensing circuit, as disclosed in Japanese Published Examined (Kokoku) Patent Appli. No. 29-8000. In this oscillator, the electrode 1A is connected in parallel to a coil 15 having a tap 15 connected to a cathode of a vacuum bulb 16 so as to form a resonance circuit composed of parallel-connected electrode capacitor 1 and the coil 15. Further, an end of the coil 15 is connected to a grid of the same vacuum tube 16. To detect the oscillator signal, another coil 17 is induction-coupled to the coil 15 so that an output signal whose frequency changes according to the electrode capacitor 1 can be outputted.

FIG. 3 shows another classical oscillator capacitance sensing circuit, as disclosed in Japanese Published Examined (Kokoku) utility Model Appli. No. 44-17838. In this oscillator, a feedback loop formed between a plate and a cathode of a vacuum bulb 18 is composed of a capacitor 21, a resistor 22, a first coil 19, a second coil 20 induction-coupled to the first coil 19, and a parallel-connected resistor and capacitor. The electrode capacitor 1 is connected in parallel to the first coil 19 so as to form a parallel resonance circuit. In this circuit, the frequency of the oscillation signal obtained through the plate of the vacuum bulb 18 changes according to the electrode capacitance $C_1$. Further, to detect the oscillator signal, a grid of another vacuum bulb 24 is connected to the plate of the bulb 18 via a capacitor 21 and a resistor 23 so that an output signal can be outputted after having been amplified by the bulb 24.

In the prior-art oscillator capacitance sensing circuits, however, there exists a problem in that the sensing reliability is poor, because a bias voltage of an active element is directly applied to the electrode 1A within which a substance to be measured is disposed.

In more detail, in FIG. 1(a) a bias voltage applied to the base of the transistor 9 is applied to the electrode 1A via the capacitor 4; in FIG. 2 a bias voltage applied to the grid of the bulb 16 is directly applied to the electrode 1A; and in FIG. 3, a bias voltage applied to the grid of the bulb 24 is applied to the electrode 1A. Therefore, there exists a problem in that the electrode plates are subjected to electrolytic corrosion due to a relatively high dc bias voltage applied to the active element (i;e. transistor, bulb, etc.) which constitutes an oscillator circuit.

This is because when a relatively high dc voltage is applied to the electrode 1A, since ions are dissolved into the substance 2 to be measured, the substance 2 changes to an electrolytic solution, so that an electromotive force is generated between the two electrode plates to cause electrolytic corrosion.

Here, in FIG. 1(a), it should be noted that although a capacitance 4 is connected in series between the electrode capacitor 1 and the coil 6, since the capacitor 5 is connected in parallel to the series-connected two capacitors 1 and 4, a high bias voltage is still applied to the electrode 1A.

SUMMARY OF THE INVENTION

With these problems in mind therefore, it is the primary object of the present invention to provide an electrostatic capacity sensing circuit of high detection reliability, without being subjected to the bias voltage of the active element of the oscillator.

To achieve the above-mentioned object, the electrostatic capacitance sensing circuit according to the present invention comprises: (a) resonance means having an electrode capacitance formed by a substance to be measured and an inductance at least a part of which is connected in parallel to the electrode capacitance; (b) active element means oscillating at a resonance frequency determined by said resonance means; and (c) capacitive coupling means connected between said resonance means and said active element means.

In the electrostatic capacitance sensing circuit of the present invention, since at least part of the inductance having a small resistance is connected in parallel to the electrode capacitance including a substance to be measured and additionally the resonance means is coupled to the active element means via the capacitive coupling means, it is possible to prevent a bias voltage applied to the active element means from being directly applied to the electrode. This is because since the resistance of the inductance (i.e. coil) is small, the voltage applied across the electrode capacitance can be reduced. Therefore, it is possible to effectively protect the electrode plate from electrolytic corrosion, thus improving the sensor reliability.

DETAILED DESCRIPTION OF THE PREFERRED EMBODIMENTS

A first embodiment of the electrostatic capacity sensing circuit according to the present invention will be described in more detail hereinbelow with reference to the attached drawings.

Figure 4A:
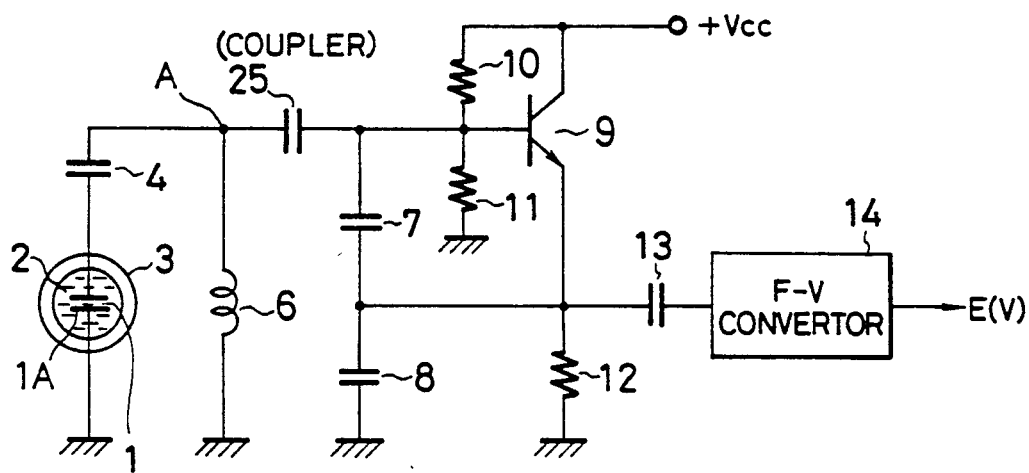
FIG. 4(a) is a circuit diagram showing a first embodiment of the electrostatic capacitance sensing circuit according to the present invention.
Figure 4B:
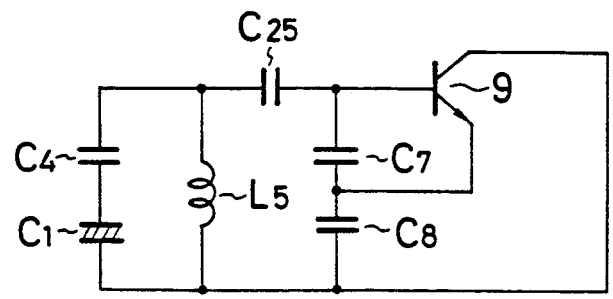
FIG. 4(b) an equivalent circuit diagram of that shown in FIG. 4(a)

FIG. 4(a) is a Clapp oscillation circuit diagram of the capacitance sensing circuit of the present invention and FIG. 4(b) is an equivalent circuit thereof. In comparison of the circuit shown in FIG. 4(a) with that shown in FIG. 1(a), the differences between the two are that the inductor 6 of the prior-art Clapp circuit is replaced with a capacitive coupler (capacitor) 25 and the capacitor 5 of the prior-art Clapp circuit is replaced with the inductor 6.

Figure 1A:
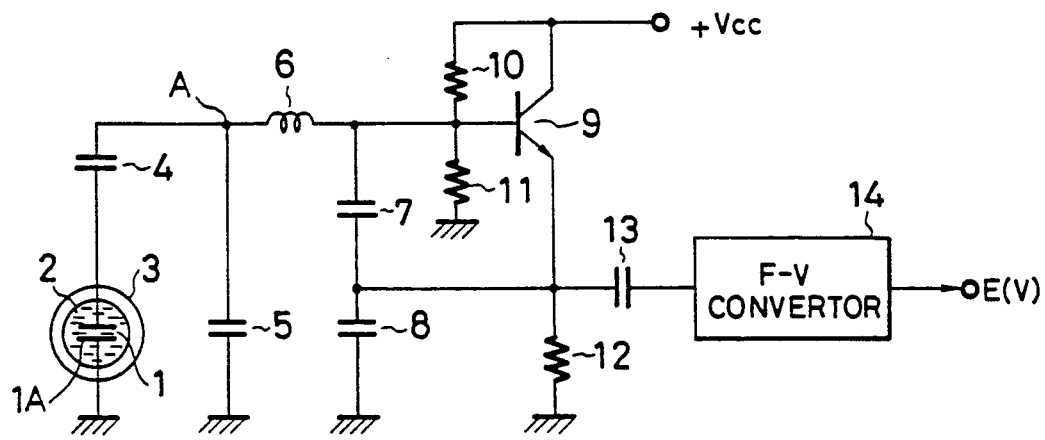
FIG. 1(a) is a circuit diagram showing a first prior-art electrostatic capacitance sensing circuit.
Figure 1B:
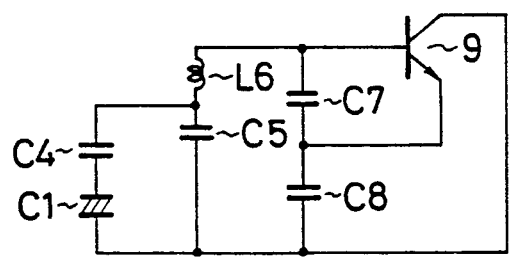
FIG. 1(b) is an equivalent circuit diagram of that shown in FIG. 1(a)
Figure 1C:
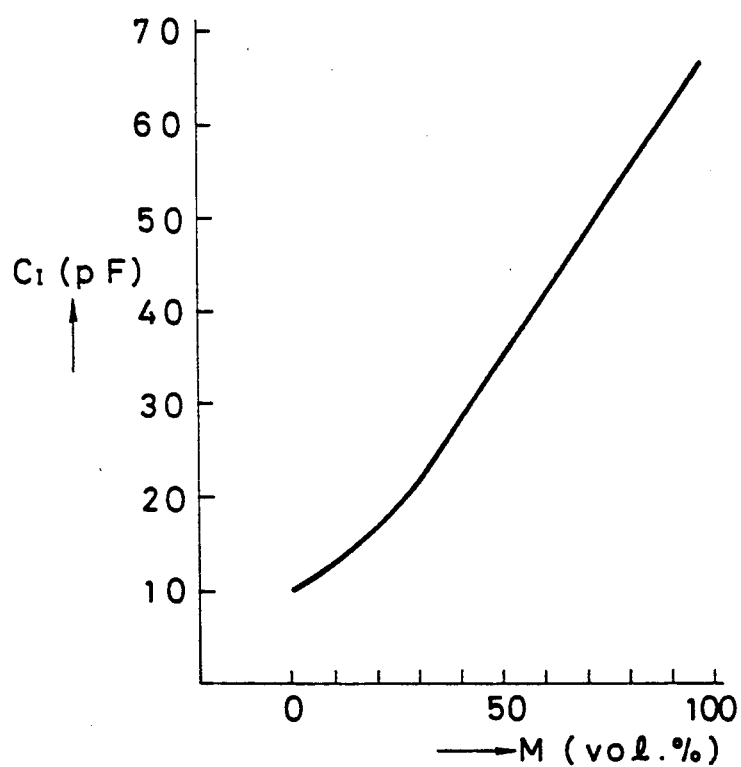
FIG. 1(c) is a graphical representation showing the relationship between the electrode capacitance and the methanol concentration.
Figure 2:
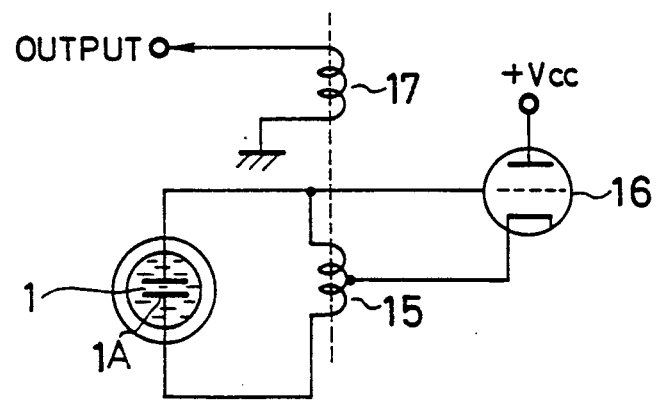
FIG. 2 is a circuit diagram showing a second prior-art electrostatic capacitance sensing circuit.
Figure 3:
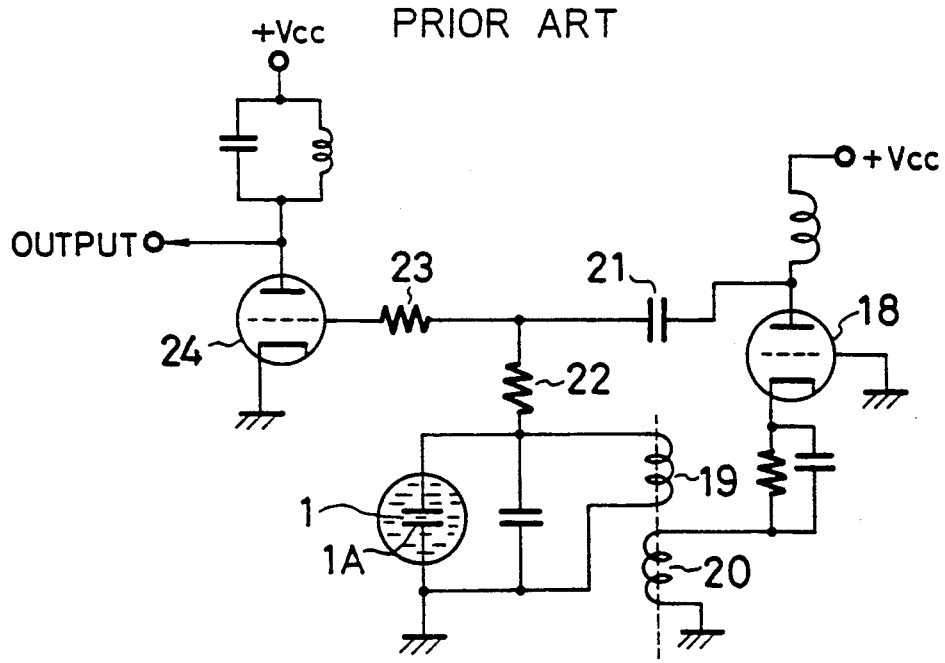
FIG. 3 is a circuit diagram showing a third prior-art electrostatic capacitance sensing circuit.

In FIG. 1(a), since the point A is connected to the ground via capacitors 4, 1, and 5, the potential at point A is almost equal to the bias voltage applied to the base of the transistor 9. On the other hand, in FIG. 4(a), since the point A is connected to the ground via an inductance having a small resistance, the potential at point A is very low, thus preventing a high bias voltage from being applied to the electrode 1A.

In more detail, the electrode 1 is connected in series with a capacitor 4. The series-connected electrode capacitor 1 and capacitor 4 are connected in parallel to the inductor 6. Therefore, a parallel resonance circuit composed of the parallel connected electrode capacitor 1 and inductor 6 are electrostatically coupled to the base of the transistor 9 via a capacitive coupler (i.e. capacitor) 25. The circuit configuration and the functional effects of this embodiment are substantially the same as in the case with the prior-art Clapp circuit shown in FIG. 1(a).

In this embodiment, since the capacitors 1 and 4 and the inductance 6 are connected in parallel, the oscillation frequency $f_{01}$ of the oscillator can be expressed as $$f_{01} = \frac{1}{2\pi \sqrt{L_6 \left( \dfrac{C_1 C_4}{C_1 + C_4} + \dfrac{C_7 C_8 C_{25}}{C_7 C_8 + C_7 C_{25} + C_8 C_{25}} \right)}} \quad (3)$$

where $C_4$, $C_7$, $C_8$ and $C_{25}$ denote the capacitances of capacitors 4, 7, 8 and 25 and $L_6$ denotes the inductance of the coil 6, as shown in FIG. 4(b).

The oscillator signal is applied to the F-V convertor 14 via a capacitor 13 in the same way as in FIG. 1(a).

In the sensing circuit shown in FIG. 4(a), a bias voltage of about Vcc/2 is required to be applied to the emitter of the transistor 9. If Vcc is 5V, the bias voltage is about 2.5 V. Here, the assumption is made that the forward voltage between the base and the emitter is 0.7 (V), a voltage of 3.2 V (=2.5+0.7) is applied to the base as a bias voltage. Therefore, although a dc voltage of about 3.2 V is directly applied to the capacitor (capacitive coupler) 25, however, since the dc resistance of the coil 6 connected in parallel to the electrode capacitance $C_1$ is extremely small (e.g. 0.1 ohms), almost zero dc voltage is applied to the point A of the oscillator circuit. Therefore, although the resonance circuit of the oscillator is composed of parallel-connected electrode capacitance $C_1$ and inductance $L_6$, almost no dc voltage is applied to the electrode 1, so that it is possible to prevent the electrode from electrolytic corrosion, thus increasing the capacitance sensing reliability.

The presence of the capacitor 4 connected in series with the electrode 1A also serves to prevent the electrode 1A from electrolytic corrosion. In more detail, the electrode plates of the electrode 1A is usually made of a corrosion-resistant metal such as stainless (SUS 304) or covered with pure nickel plating. However, in some cases, the electrode plates are made of other metals. Therefore, there exists a problem in that various ions are dissolved into a substance 2 to be measured, with the result that electromotive force is generated between the two electrode plates with the substance 2 to be measured as electrolyte, thus resulting in electrode plate errosion. The presence of the two series connected capacitors 4 and 25 serve to prevent a dc voltage from being applied to the electrode 1A and further the presence of the inductance 6 serves to reduce the dc voltage applied across the series connected capacitors 1 and 4, thus protecting the electrode from electrolytic corrosion.

Figure 5:
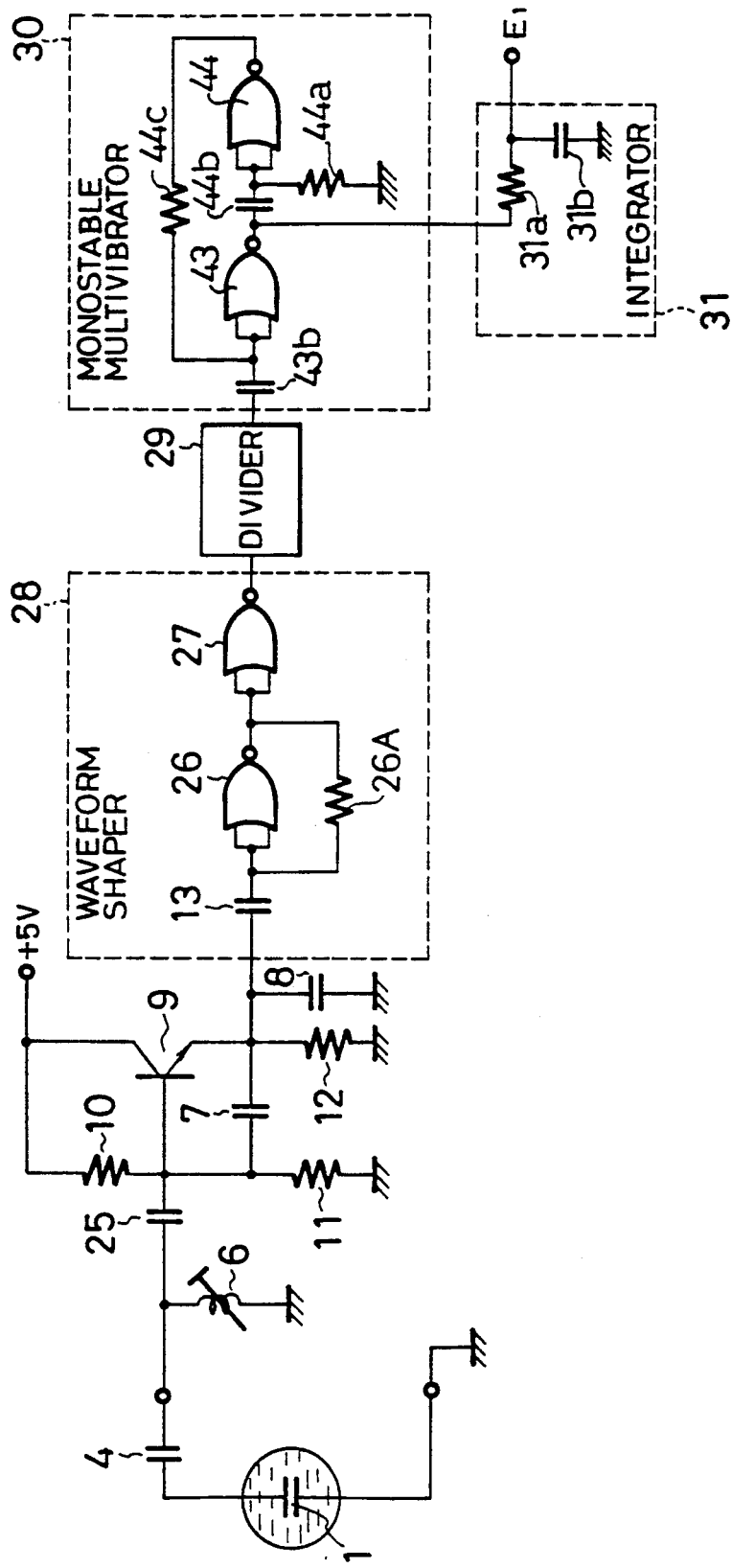
FIG. 5 is a practical circuit diagram of that shown in FIG. 4(a)

FIG. 5 is a more practical circuit in which the coil 6 is a variable inductance coil, and further the F-V connector 14 is composed of a waveform shaper 28, a divider 29, a monostable multivibrator 30, and an integrator 31. The waveform shaper 28 is composed of two NOR gates 26 and 27, and a feedback resistor 26a. The monostable multivibrator 30 is composed of two NOR gates 43 and 44, two capacitors 43b and 44b, and two resistors 44a and 44c. The integrator 31 is composed of a resistor 31a and a capacitor 31b.

In operation, the oscillation signal outputted from the emitter of the transistor 9 is inputted to two inputs of the first-stage NOR gate 26 having a feedback resistor 26a and then to the two inputs of the second-stage NOR gate 27, so that the oscillator sine waveform is shaped into a square waveform. The frequency to the waveformed pulse signal is divided into $f_0/10$, for instance through the divider 29, so that the oscillator pulse signal can be processed at low speed. The divided oscillator pulse signal is than inputted to the monostable multivibrator 30 so as to be transformed into pulse signals whose duty ratio (i.e. pulse width) is roughly proportional to the divided frequency $f_0/10$. The output signal from the monostable multivibrator 30 is integrated through the integrator 31, so that a dc output signal E(V) whose dc level is roughly proportional to the oscillator frequency $f_0/10$ can be outputted as an output signal E(V).

Figure 6A:
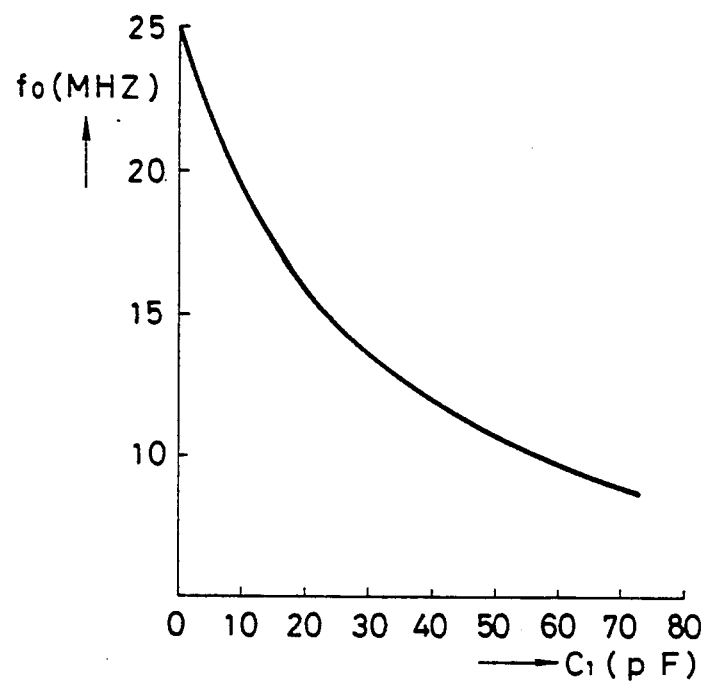
FIG. 6(a) is a graphical representation showing the relationship between the electrode capacitance and the oscillation frequency of the circuit shown in FIG. 5.
Figure 6B:
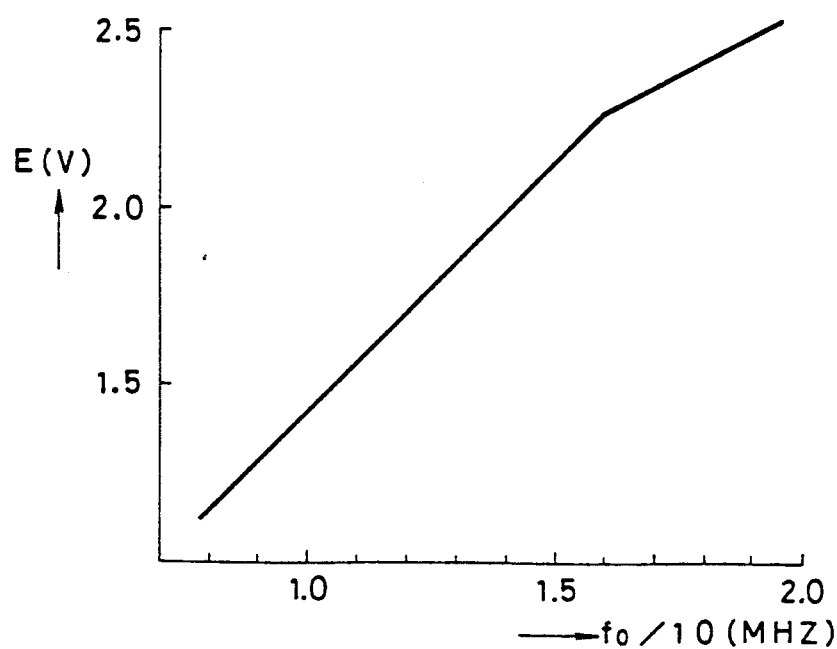
FIG. 6(b) is a graphical representation showing the relationship between the oscillation frequency and the dc output voltage.
Figure 6C:
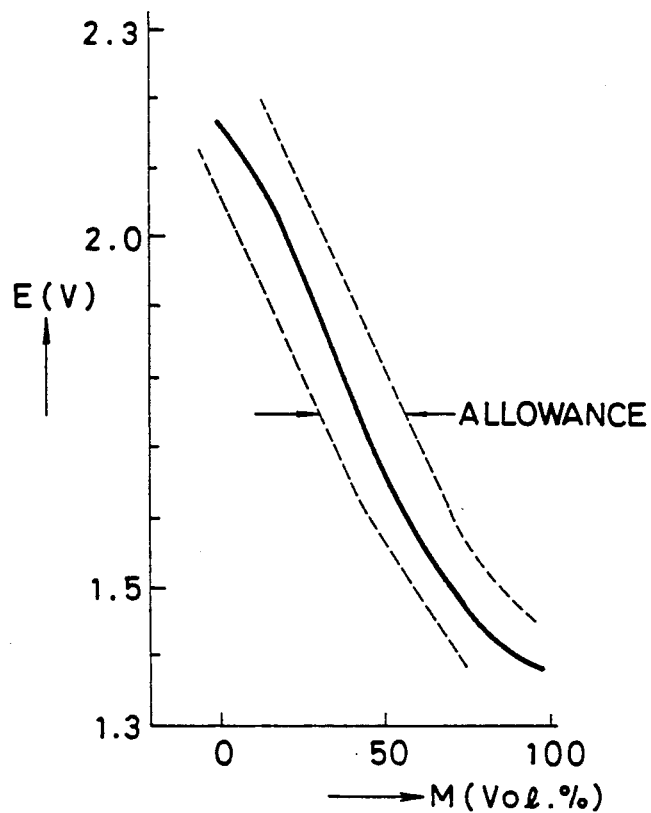
FIG. 6(c) is a graphical representation showing the relationship between the methanol concentration and the dc output voltage.
Figure 6D:
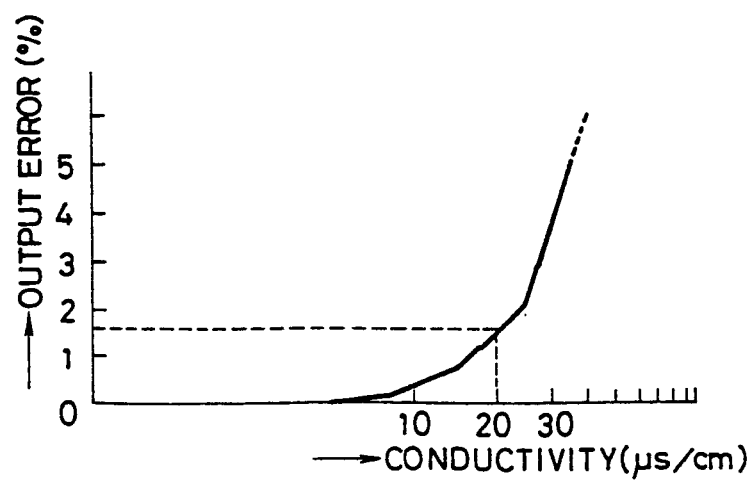
FIG. 6(d) is a graphical representation showing the relationship between the electrode conductivity and the output error percentage.

Further, FIG. 6(a) shows an example of the relationship between the electrode capacitance $C_1$ (pF) and the oscillation frequency $f_0$ (MHz), FIG. 6(b) shows an example of the relationship between the divided oscillator frequency $f_0/10$ (MHz) and the output voltage E(V); FIG. 6(c) shows an example of the relationship between the methanol concentration M (vol. %) and the output voltage E(V) in which two dashed lines indicate an allowable range of the output voltage E(V) relative to the methanol concentration M (vol. %), by way of example; and FIG. 6(d) shows an example of the relationship between the conductivity ($\mu$s/cm) of the substance to be measured and an error in the output signal voltage E(V), in which the abscissa is expressed in logarithmic scale. Further, FIG. 6(d) indicates that it is possible to reduce the error in the output voltage E(V) within a range less than 2% as far as the conductivity of the substance to be measured is about 20 $\mu$s/cm or less and further the output voltage error (%) increase with increasing conductivity of the substance to be measured in accordance with a roughly linear logarithmic function as shown in FIG. 6(d).

Figure 7:
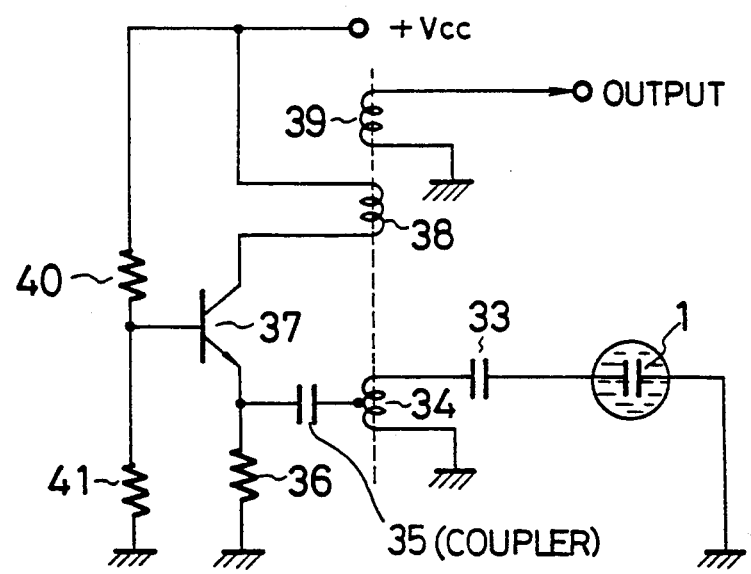
FIG. 7 is a circuit diagram showing a second embodiment of the electrostatic capacitance sensing circuit according to the present invention.

FIG. 7 shows a second embodiment of the sensing circuit according to the present invention, in which a series resonance circuit composed of an electrode capacitor 1 and the inductor (coil) 34 is connected to the emitter of a transistor 37 via a capacitive coupler (capacitor) 35. In this embodiment, a part of the coil 34 is connected in parallel to the series-connected electrode capacitor 1 and a corrosion prevention capacitor 33. In more detail, an intermediate tap of the coil 34 is connected to the emitter of a transistor 37 via the capacitive coupler 35. Further, other two coils 38 and 39 are wound around and overlapped with the resonance coil (inductor) 34. The coil 38 is connected between the supply voltage Vcc and the collector of the transistor 37, and the coil 39 is connected between an output terminal and the ground. The emitter of the transistor 37 is biased by a resistor 36 and the base of the transistor 37 is biased by two resistors 40 and 41, respectively.

In this circuit configuration, the electrode capacitor 1 and the coil 34 form a series resonance circuit, and the inductive voltage generated by the coil 34 is transmitted to the coils 38 and 39 though induction coupling, so that the collector voltage can be feedbacked to the emitter of the transistor 37 for oscillation. The oscillation frequency $f_0$ can be roughly expressed as $$f_0 = \frac{1}{2\pi \sqrt{L_{34} \cdot C_1}} \qquad (4)$$

where $L_{34}$ denotes the inductance of the coil 34 and $C_1$ denotes the electrostatic electrode capacitance.

The oscillation signal can be outputted through the coil 39 induction coupled to the coil 34. Therefore, in this embodiment, since the frequency of the oscillation signal changes according to the value of the electrode capacitance $C_1$, it is possible to measure the dielectric constant of a substance or the concentration of the methanol to be measured. In the same way, since the electrode 1A is not directly connected to the emitter and the collector of the transistor 37, and further a part of the coil 34 is connected in parallel to the electrode capacitor 1, it is possible to prevent a bias voltage of the transistor 37 from being applied to the electrode 1 to protect the electrode from electrolytic errosion.

As described above, in the electrostatic capacitance sensing circuit according to the present invention, since a resonance circuit is composed of an electrode capacitance (including two opposing electrode plates between which a substance to be measured is sandwiched) and an inductance at least part of which is connected in parallel to the electrode capacitance and additionally the resonance circuit is capacitivity coupled to the active element constituting an oscillator circuit via a capacitor, it is possible to effectively prevent dc bias voltage of the active oscillator element from being applied to the electrode 1, thus improving the reliability and durability of the electrode plates without being subjected to electrolytic corrosion.

What is claimed is:

1. An electrostatic capacitance sensing circuit, comprising;
   (a) resonance means having an electrode capacitance formed by a substance to be measured, a corrosion preventing capacitor for preventing electrolytic corrosion connected in series with the electrode capacitance with respect to a junction point, and an inductance connected to the electrode capacitance and said corrosion preventing capacitor via said junction point;

(b) active element means oscillating at a resonance frequency predetermined by said resonance means; and (c) capacitive coupling means connected between said junction point of the inductance and the corrosion preventing capacitor and said active element means to prevent a DC voltage from being applied to the electrode capacitance.

2. The electrostatic capacitance sensing circuit of claim 1, wherein said resonance means comprises:
(a) a vessel; and
(b) a pair of opposing electrode plates for sandwiching a substance to be measured therebetween within said vessel.

3. The electrostatic capacitance sensing circuit of claim 1, wherein said resonance means is a parallel resonance circuit in which the capacitance and the inductance are connected in parallel to each other with respect to said junction point.

4. An electrostatic capacitance sensing circuit, comprising:
(a) resonance means having an electrode capacitance formed by a substance to be measured, a corrosion preventing capacitor for preventing electrolytic corrosion connected in series with the electrode capacitance, and an inductance connected to the electrode capacitance and said corrosion preventing capacitor;
(b) active element means oscillating at a resonance frequency determined by said resonance means; and
(c) capacitive coupling means connected between an intermediate tap of said inductance and said active element means to prevent a DC voltage from being applied to the electrode capacitance.

5. The electrostatic capacitance sensing circuit of claim 1, wherein said resonance means is connected to a feedback loop of said active element means via said capacitive coupling means.

6. The electrostatic capacitance sensing circuit of claim 1, which further comprises a frequency-voltage convertor connected to said active element means.

7. The electrostatic capacitance sensing circuit of claim 6, wherein said frequency-voltage convertor comprises:

(a) a waveform shaper for waveform-shaping an oscillation signal of said active element means;
(b) a divider for dividing the frequency of the waveformed shaped oscillation signal;
(c) a monostable multivibrator for outputting a pulse signal whose duly ratio varies according to the frequency of the oscillation signal; and
(d) an integrator for integrating the pulse signal outputted from the monostable multivibrator to generate a dc signal whose voltage level is roughly proportional to the frequency of the oscillation signal.

8. The electrostatic capacitance sensing circuit of claim 7, wherein said frequency-voltage convertor is connected to said active element means via a capacitor.

9. The electrostatic capacitance sensing circuit of claim 7, wherein said frequency-voltage convertor is connected to said active element means via an inductor.

10. The electrostatic capacitance sensing circuit of claim 4, wherein said resonance means is a series resonance circuit in which the capacitance and inductance are connected substantially in series with each other.

11. The electrostatic capacitance sensing circuit of claim 4, wherein said resonance means is connected to a feedback loop of said active element means via said capacitive coupling means.

12. The electrostatic capacitance sensing circuit of claim 4, which further comprises a frequency-voltage converter connected to said active element means.

13. The electrostatic capacitance sensing circuit of claim 12, wherein said frequency-voltage convertor comprises:

(a) a waveform shaper for waveform-shaping an oscillation signal of said active element means;
(b) a divider for dividing the frequency of the waveformed shaped oscillation signal;
(c) a monostable multivibrator for outputting a pulse signal whose duty ratio varies according to the frequency of the oscillation signal; and
(d) an integrator for integrating the pulse outputted from the monostable multivibrator to generate a dc signal whose voltage level is roughly proportional to the frequency of the oscillation signal.

14. The electrostatic capacitance sensing circuit of claim 13, wherein said frequency-voltage convertor is connected to said active element means via an inductor.

15. The electrostatic capacitance sensing circuit of claim 13, wherein said frequency-voltage convertor is connected to said active element means via an inductor.

* * * * *